(12) United States Patent
McBrady et al.

(10) Patent No.: US 8,241,919 B2
(45) Date of Patent: Aug. 14, 2012

(54) GAS PULSE GENERATOR FOR BASELINE DRIFT CORRECTION AND RELATED SYSTEM AND METHOD

(75) Inventors: Adam Dewey McBrady, Minneapolis, MN (US); J. David Zook, Golden Valley, MN (US); Alex Gu, Plymouth, MN (US); Michael L. Rhodes, Richfield, MN (US)

(73) Assignee: Honeywell International Inc., Morristown, NJ (US)

( * ) Notice: Subject to any disclaimer, the term of this patent is extended or adjusted under 35 U.S.C. 154(b) by 413 days.

(21) Appl. No.: 12/260,007

(22) Filed: Oct. 28, 2008

(65) Prior Publication Data
US 2010/0101301 A1  Apr. 29, 2010

(51) Int. Cl.
*G01N 33/00* (2006.01)
(52) U.S. Cl. ........ 436/178; 436/177; 436/174; 73/23.21
(58) Field of Classification Search .................. 436/178, 436/177, 174; 73/23.21
See application file for complete search history.

(56) References Cited

U.S. PATENT DOCUMENTS

| | | | |
|---|---|---|---|
| 4,944,035 A | 7/1990 | Aagardl et al. | |
| 6,393,894 B1 | 5/2002 | Bonne et al. | |
| 6,792,794 B2 | 9/2004 | Bonne et al. | |
| 7,000,452 B2 | 2/2006 | Bonne et al. | |
| 7,104,112 B2 | 9/2006 | Bonne | |
| 2004/0129057 A1 | 7/2004 | Bonne et al. | |
| 2004/0224422 A1 | 11/2004 | Bonne et al. | |
| 2005/0042139 A1 | 2/2005 | Bonne | |
| 2005/0063865 A1 | 3/2005 | Bonne et al. | |
| 2005/0142662 A1 | 6/2005 | Bonne | |
| 2007/0051163 A1* | 3/2007 | Wohltjen | 73/31.07 |

* cited by examiner

*Primary Examiner* — Christine T Mui

(57) ABSTRACT

A method includes acquiring a chemical sample and modulating the chemical sample at a frequency greater than a drift frequency of a sensor. The method also includes determining at least one of a presence and a concentration of the analyte within the modulated chemical sample using the sensor. Modulating the chemical sample could include alternately absorbing at least some of the analyte into a sorbent material and releasing at least some of the analyte from the sorbent material. Modulating the chemical sample could also include heating the sorbent material, absorbing part of the analyte into the sorbent material, and passing a remaining portion of the analyte into the sensor. Modulating the chemical sample could further include stopping the heating of the sorbent material, releasing the part of the analyte from the sorbent material, and passing the sample with the released part of the analyte into the sensor.

22 Claims, 6 Drawing Sheets

GAS PULSE GENERATOR FOR BASELINE DRIFT CORRECTION AND RELATED SYSTEM AND METHOD

TECHNICAL FIELD

This disclosure relates generally to chemical detection and more specifically to a gas pulse generator for baseline drift correction and related system and method.

BACKGROUND

Chemical sensors are routinely used to detect the presence and measure the concentration of various chemicals. Example structures and processes related to gas detectors are disclosed in U.S. Pat. No. 6,393,894 and U.S. Pat. No. 4,944,035, which are hereby incorporated by reference. However, many chemical sensors experience baseline drift over the course of their operation.

This drift manifests itself by causing a sensor to report a chemical concentration that is an inaccurate measure of the true chemical concentration. For example, if a sensor's baseline response drifts to a value one unit higher than typical, the sensor will report a chemical concentration of one even if the true chemical concentration is zero. Baseline drift requires the sensor to either be re-calibrated frequently using a reference gas source in order to establish a proper baseline or the use of a poorer sensitivity that accounts for the expected drift. These caveats severely limit the applications for the sensor to those in which signals are well above the baseline drifts between calibrations.

SUMMARY

This disclosure provides a gas pulse generator for baseline drift correction and related system and method.

In a first embodiment, a method includes acquiring a chemical sample and modulating the chemical sample at a frequency greater than a drift frequency of a sensor. The method also includes determining at least one of a presence and a concentration of the analyte within the modulated chemical sample using the sensor.

In particular embodiments, modulating the chemical sample includes alternately absorbing at least some of the analyte into a sorbent material and releasing at least some of the analyte from the sorbent material.

In a second embodiment, a system includes a pump configured to obtain a chemical sample and a pulse generator configured to modulate the chemical sample to produce a modulated chemical sample. The system also includes a sensor configured to detect at least one of a presence and a concentration of an analyte within the modulated chemical sample. The pulse generator is configured to modulate the chemical sample to produce the modulated chemical sample at a frequency greater than a drift frequency of the sensor. In addition, the system includes a controller configured to accept an output signal from the sensor and to determine an actual concentration of the analyte within the chemical sample.

In a third embodiment, a method includes acquiring a chemical sample. The method also includes modulating the chemical sample by alternately heating and cooling the sample at a frequency higher than a baseline drift of a sensor. The method further includes determining a concentration of the analyte within the modulated chemical sample using the sensor.

Other technical features may be readily apparent to one skilled in the art from the following figures, descriptions, and claims.

BRIEF DESCRIPTION OF THE DRAWINGS

For a more complete understanding of this disclosure, reference is now made to the following description, taken in conjunction with the accompanying drawings, in which.

DETAILED DESCRIPTION

FIGS. 1 through 6, discussed below, and the various embodiments used to describe the principles of the present invention in this patent document are by way of illustration only and should not be construed in any way to limit the scope of the invention. Those skilled in the art will understand that the principles of the invention may be implemented in any type of suitably arranged device or system.

As noted above, chemical sensors typically experience baseline drift over the course of their operation. This disclosure provides a mechanism for providing baseline drift correction to a chemical sensor by providing an input having a modulated analyte concentration that varies from low to high concentrations. This modulation allows for the sensor to be calibrated for the difference between those signals. The difference is unrelated and unaffected by baseline drift.

Figure 1:
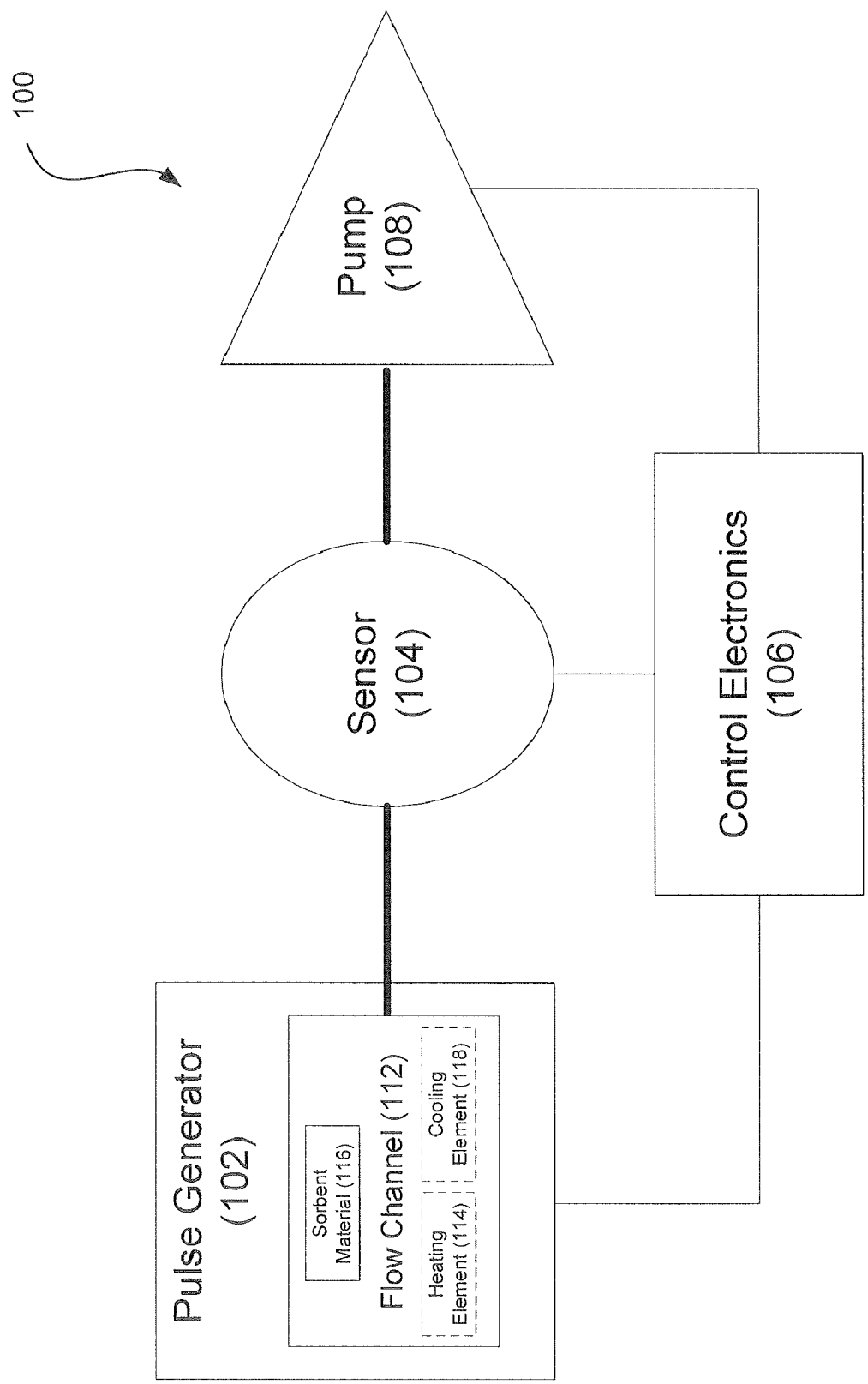
FIG. 1 illustrates an example baseline drift correction system for a chemical sensor according to one embodiment of this disclosure.

FIG. 1 illustrates an example baseline drift correction system 100 for a chemical sensor according to one embodiment of this disclosure. The embodiment of the baseline drift correction system 100 shown in FIG. 1 is for illustration only. Other embodiments of the baseline drift correction system 100 could be used without departing from the scope of this disclosure.

As shown in FIG. 1, the baseline drift correction system 100 includes a pulse generator 102, a chemical sensor 104, control electronics 106, and a pump 108. In this example, a sample is provided to the pulse generator 102 and leaves the system 100 through the pump 108.

In this embodiment, the pulse generator 102 modulates the chemical concentrations input to the sensor 104 by providing a sorbent material 116 in conjunction with one or more heating elements 114. The heating elements 114 can rapidly change the temperature of the sorbent material 116 (which may or may not be in an array format). The sorbent material 116 represents a material that may be designed to absorb a specific chemical agent or "analyte." The determination of what type of sorbent material 116 to use within the pulse generator 102 depends upon the specific chemical agent that the system 100 is designed to detect. Example sorbent materials may include selective or universal fibrous compounds, polymers, or any other substance(s) capable of absorbing and releasing chemical agents.

The sorbent material 116 is contained within the flow channel 112. The heating element 114 is in close proximity and ideally in good thermal contact with the sorbent material 116. The flow channel 112 connects a sample intake to the chemical sensor 104. When the heating element 114 is inactive, the sorbent material 116 may absorb any analyte passing through the flow channel 112. Activation of the heating element 114 causes the absorbed analyte to leave the sorbent material 116 and exit the flow channel 112. When the heating element 114 is active, the concentration of the analyte leaving the flow channel 112 is higher than the concentration of the analyte in the original sample as it entered the pulse generator 102. The activation of the heating element 114 can be followed by a period of inactivation of the heating element 114, resulting in a low analyte concentration exiting the flow channel 112 (as the analyte is being absorbed up by the now-regenerated sorbent material 116). When heating element 114 is inactive, cooling element 118 may be active. Cooling element 118 may be any structure that is suitable to cool the sorbent material 116. Repeating this process generates a train of sample pulses for the chemical sensor 104 that alternate between higher and lower concentrations than the nominal analyte being analyzed. While FIG. 1 illustrates both a heating element 114 and a cooling element 118, the system 100 could include only one of these elements. For example, passive cooling may occur without cooling element 118 when heating element 114 is not active. It understood that system 100 might include only cooling element 118, only heating element 114, or both cooling element 118 and heating element 114.

As a result, the samples being passed into the sensor 104 are artificially higher and lower in concentration than the actual concentration of the analyte. These "higher" and "lower" concentrations are relative to the actual concentration of the analyte present and are not meant to imply any specific range of concentrations. Since higher and lower concentrations of the analyte are known and the relationship of these higher and lower values to the actual concentration of the analyte is known, determining the actual concentration of the analyte may be reliably preformed even during periods of baseline drift without the need to perform additional calibrations of the sensor 104.

The higher and lower analyte concentrations created by the pulse generator 102 are placed into the sensor 104. Through empirical measurements, the relationship between the higher and lower concentrations to the analyte concentration is known. This relationship can be stored in the control electronics 106, which can use this along with information related to the modulation (controlled by the control electronics 106) and the signal created by the sensor 104 to determine the actual concentration of analyte present. The chemical sensor 104 converts the alternating higher and lower chemical concentrations into a single reported chemical concentration. This process is analogous to optical chopping and lock-in amplification methods.

The selection of the sorbent material 116 allows for additional selectivity for the system 100. For example, the chemical sensor's output signal may be generated only for those molecules that adsorb reversibly by the sorbent material 116 within the temperature range used for cycling the heating elements 114.

The pump 108 is used here to create active sampling. Active sampling includes the drawing of samples into the system 100 from the ambient atmosphere. It is referred to as "active" because the pump 108 is being used to force samples into the system 100.

The pulse generator 102, sensor 104, and pump 108 are each controlled by the control electronics 106. The control electronics 106 may be configured to determine the maximum concentration of samples passed into the sensor 104 (the maximum signal level generated by the sensor 104) and the minimum concentration of the samples passed into the sensor 104 (the minimum signal level generated by the sensor 104). The control electronics 106 can use the minimum and maximum concentrations to determine the actual concentration of an analyte. The control electronics 106 may also be configured to take into consideration the temperature characteristics of the analyte, thereby compensating for the effects of heating and cooling the sample.

In particular embodiments, the system 100 can be implemented based on the same or similar technology used in phased heater array for enhanced detection (PHASED) chips. The PHASED chips have heaters and sorbents in an array. For example, the system 100 may use one or more heating elements 114 that can be timed with a sample flow to provide a highly concentrated 10-20 ms wide sample separated by approximately four seconds of low analyte reaching the chemical sensor 104.

Also, in particular embodiments, the system 100 may use only one sorbent-heater combination and a sampling pump 108 operating at a constant pumping speed. However, there are a wide variety of ways to combine the heater and sorbent material to produce a variety of pulsed trains of various high and low concentrations and with various high and low concentration durations.

Although FIG. 1 illustrates an example baseline drift correction system 100 for a chemical sensor, various changes may be made to FIG. 1. For example, a system could include any number of pulse generators 102, sensors 104, control electronics 106, and pumps 108. As a particular example, the control electronics 106 could be used to control multiple pulse generators 102, sensors 104, and pumps 108. Also, in other embodiments, a micro-filter rather than a sorbent material may be used to alternatively alter the amount of analyte exposed to the sensor 104.

Figure 2:
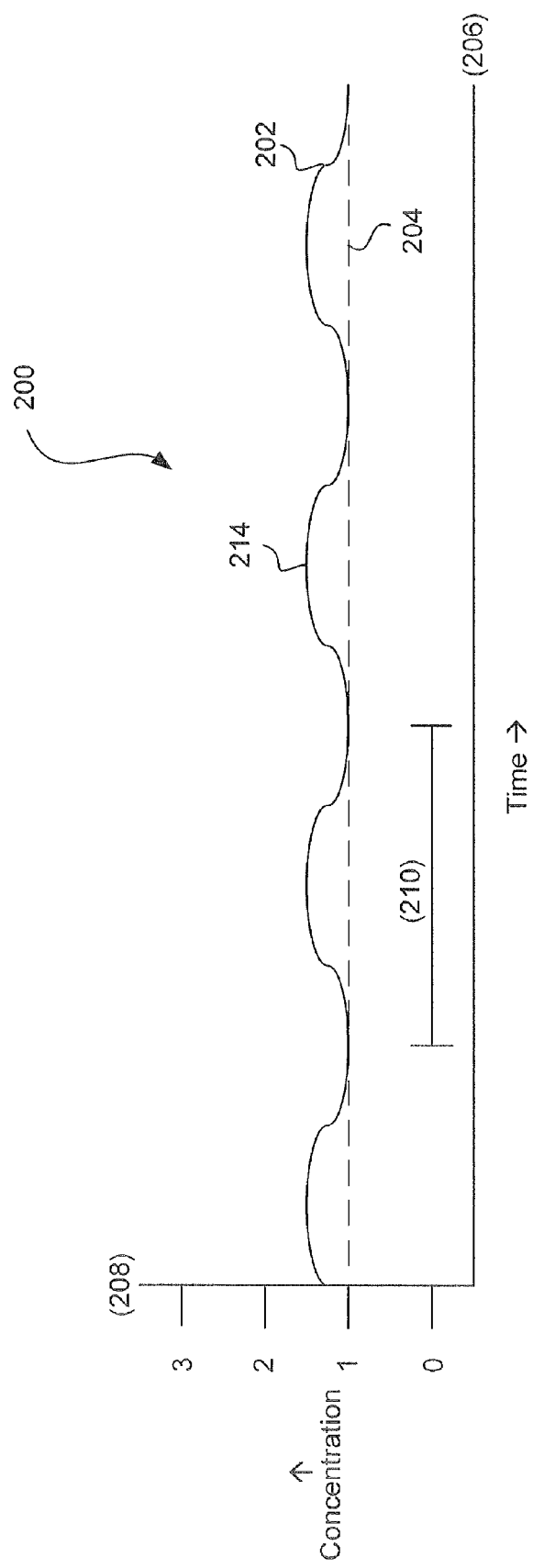
FIG. 2 illustrates an example graph of a time and signal response due to constant chemical concentration using a chemical sensor experiencing baseline drift without a pulse generator according to one embodiment of this disclosure.

FIG. 2 illustrates an example graph 200 of a time and signal response of a chemical sensor being exposed to constant chemical concentration 204 but undergoing a sinusoidal baseline drift. In this example, the graph 200 plots a sensor response 202 and an actual analyte concentration 204 in terms of concentration 208 versus time 206 for a normal sensor (without the pulse generator 102). The drift frequency 210 of the input signal based on the normal sensor response 202 shows that the sensor detects a significantly higher concentration at time 214 than is actually present. Without the pulse generator 102, the sensor may therefore report a concentration of analyte being present that is significantly higher than the actual concentration of analyte.

Figure 3:
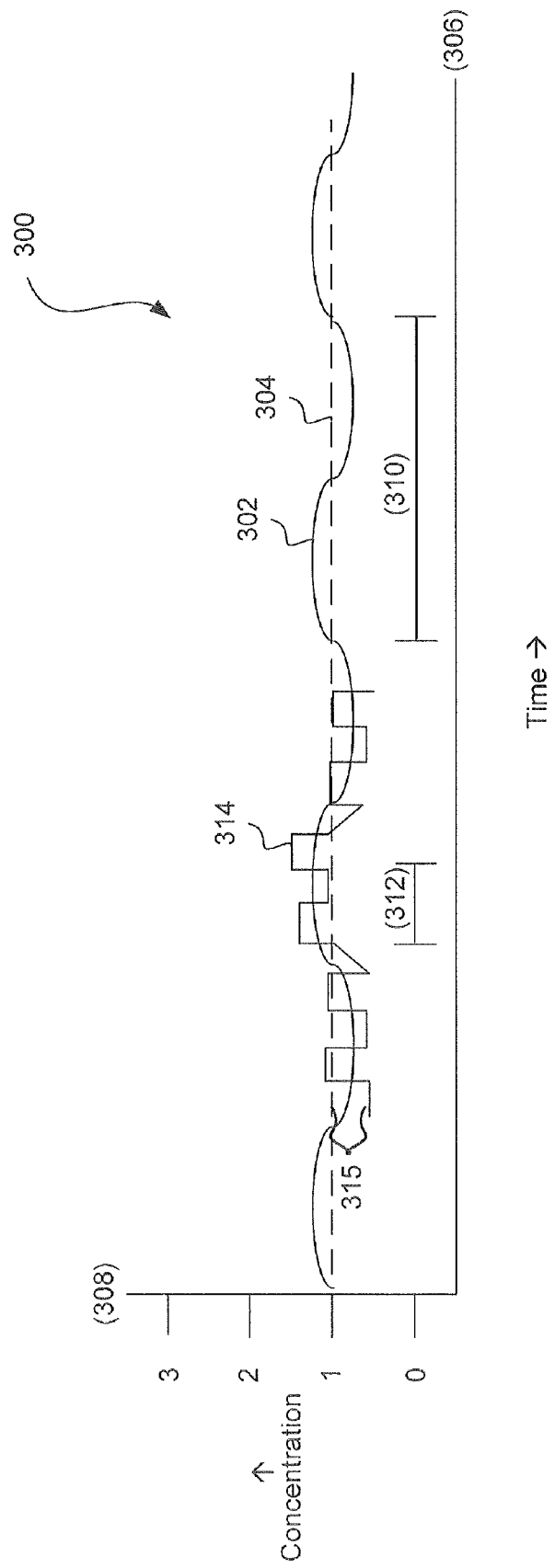
FIG. 3 illustrates an example graph of a time and signal response of a chemical sensor experiencing baseline drift with a pulse generator according to one embodiment of this disclosure.

FIG. 3 illustrates an example graph 300 of a time and signal response of a chemical sensor and a pulse generator according to one embodiment of this disclosure. In this example, the graph 300 plots a sensor response 302 and an actual analyte concentration 304 in terms of concentration 308 versus time 306 for a sensor 104 with a pulse generator 102. In this example, the difference between the high and low signal 315 remains constant and relative to the true analyte concentration 304, even as the baseline shifts. As shown here, the frequency 312 of a pulse generated signal 314 is higher than a baseline drift frequency 310. This effectively allows the calibration of the sensor to be immune to baseline drift. This calibration allows for consistent and accurate determination of the actual analyte concentration 304 using the pulse generator 102 and calibrating concentration to the high low signal difference 315.

Since the frequency of the pulse generator 102 is higher than the frequency of the baseline drift, the sensor 104 may be constantly calibrated based on the frequency of the pulse generator 102. This calibration is performed, in some embodiments, because the control electronics 106 use the frequency of the pulse generator 102 to determine the actual levels of analyte within the sample. Therefore, both the high and low concentrations of the analyte passed into the sensor 104 are enhanced. A "high" is present when the sorbent material 116 releases the analyte, and a corresponding "low" is present when the sorbent material 116 absorbs the analyte. Also, the measurement is improved since the times when the sensor 104 should detect higher and lower concentrations are known by the control electronics 106 (the control electronics 106 know when the heating element 114 is active). This information allows the control electronics 106 to accurately determine the amount of analyte present regardless of any sensor baseline drift that may have occurred.

Although FIGS. 2 and 3 illustrate example graphs of time and signal responses of two types of sensors, various changes may be made to FIGS. 2 and 3. For example, normal and improved sensing systems could have any other suitable time and signal response.

Figure 4:
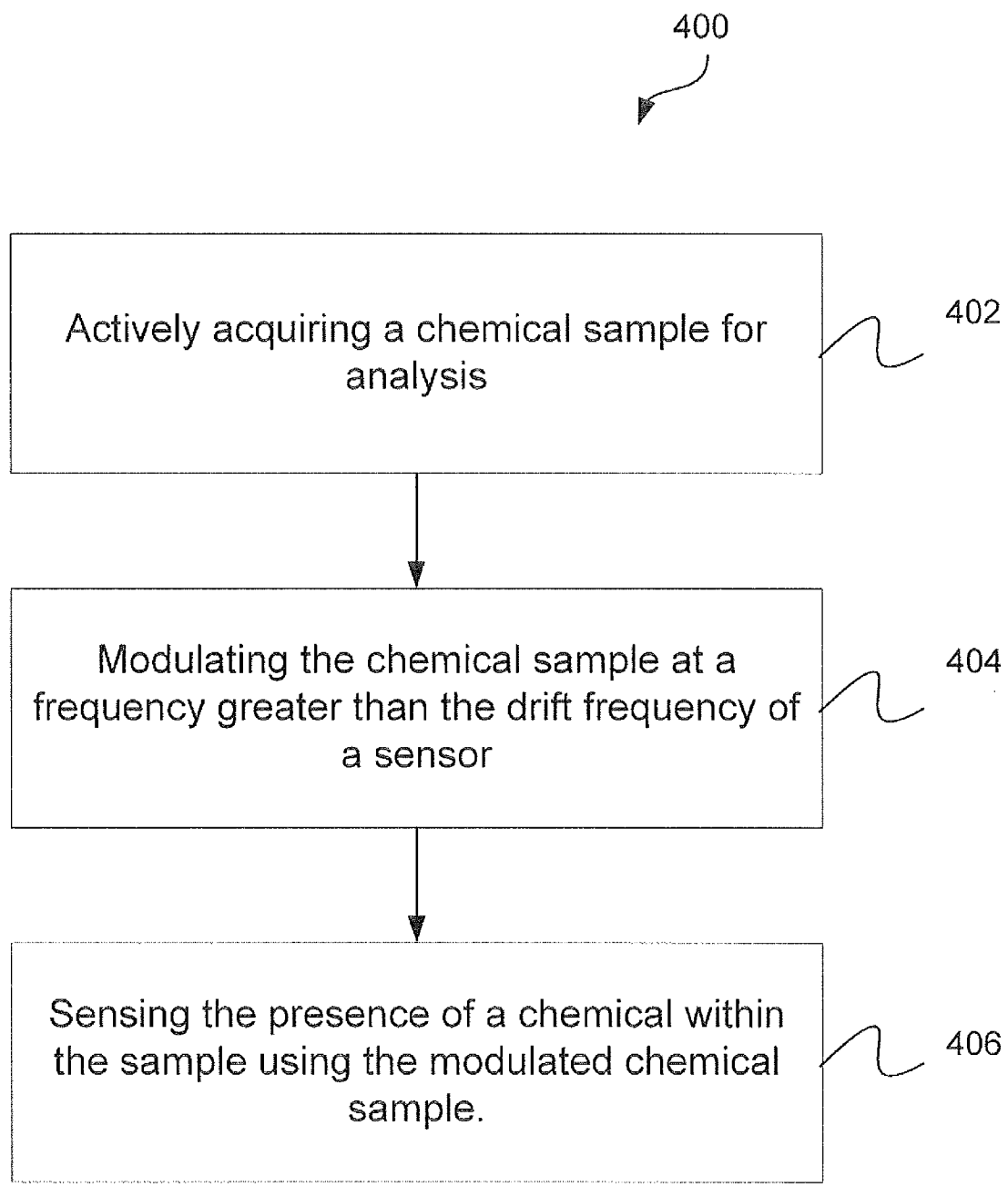
FIG. 4 illustrates an example method of using a gas pulse generator and a sensor according to one embodiment of this disclosure.

FIG. 4 illustrates an example method 400 of using a gas pulse generator and a sensor according to one embodiment of this disclosure. The embodiment of the method 400 shown in FIG. 4 is for illustration only. Other embodiments of the method 400 could be used without departing from the scope of this disclosure.

A chemical sample is actively acquired for analysis at step 402. This could include, for example, the pump 108 pulling in the sample from the ambient environment. The chemical sample is modulated at a frequency greater than the drift frequency of a sensor at step 404. This could include, for example, alternately turning the heating elements 114 on and off to increase and decrease a concentration of a chemical in the sample. The sensor then is used to sense the presence of a chemical within the sample at step 406. This could include, for example, the chemical sensor 104 generating an output signal based on the presence or concentration of a particular gas or other chemical in the sample.

Figure 5:
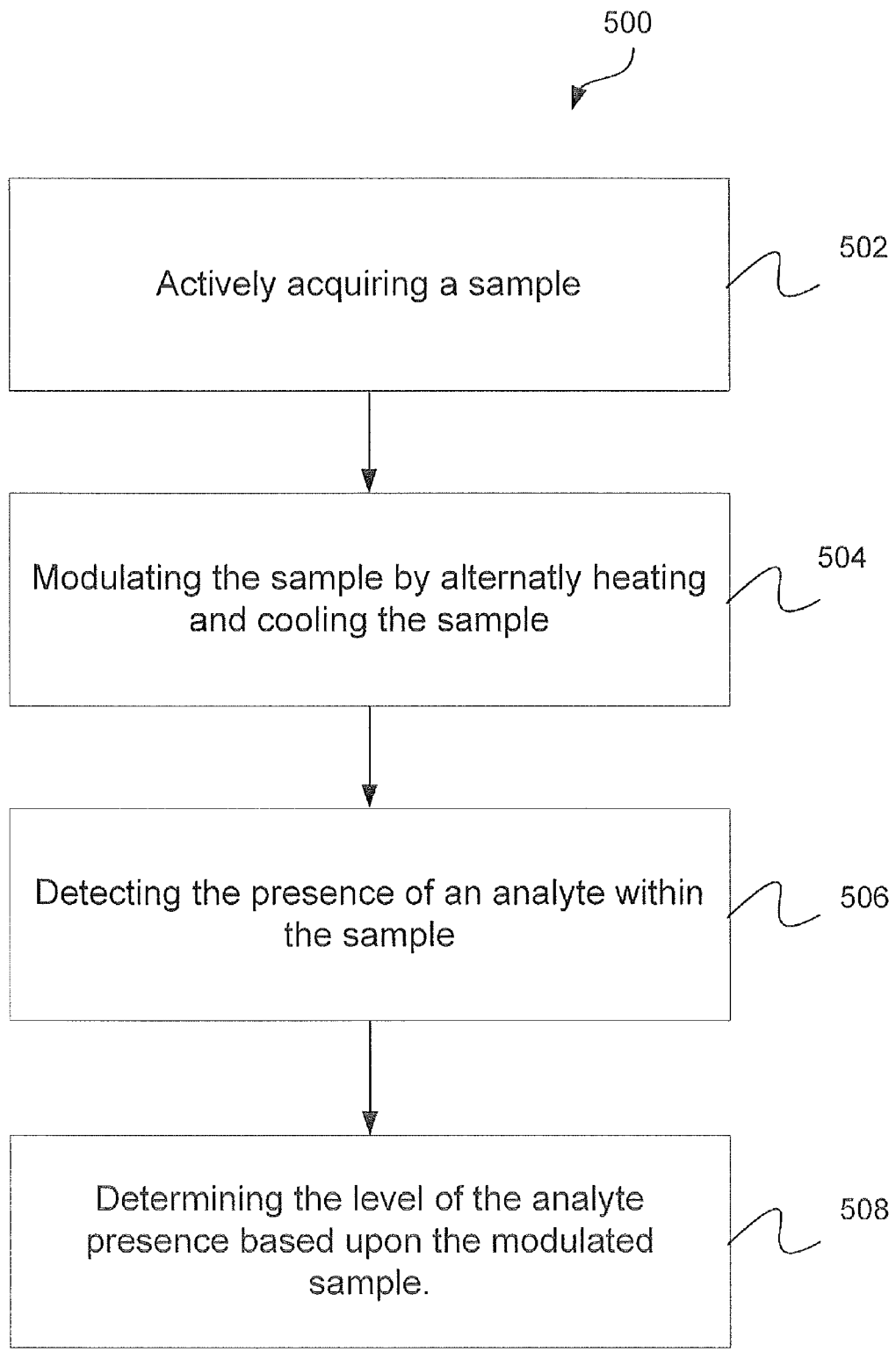
FIG. 5 illustrates an example method of correcting baseline drift using a gas pulse generator and a sensor according to one embodiment of this disclosure.

FIG. 5 illustrates an example method 500 of correcting baseline drift using a gas pulse generator and a sensor according to one embodiment of this disclosure. The embodiment of the method 500 shown in FIG. 5 is for illustration only. Other embodiments of the method 500 could be used without departing from the scope of this disclosure.

A sample is actively acquired at step 502. This could include, for example, the pump 108 pulling in the sample from the ambient environment. The sample is modulated by alternately heating and cooling the sample at step 504. This could include, for example, alternately turning the heating and/or cooling elements 114 and/or 118 on and off. A sensor detects the presence of an analyte within the sample at step 506, and the level or concentration of the analyte in the sample is determined using the modulated sample at step 508. This could include, for example, using the control electronics 106 to determine the level of analyte present.

Although FIGS. 4 and 5 illustrate example methods, various changes may be made to FIGS. 4 and 5. For example, while each figure shows a series of steps, various steps in each figure could overlap, occur in parallel, or occur multiple times.

Figure 6:
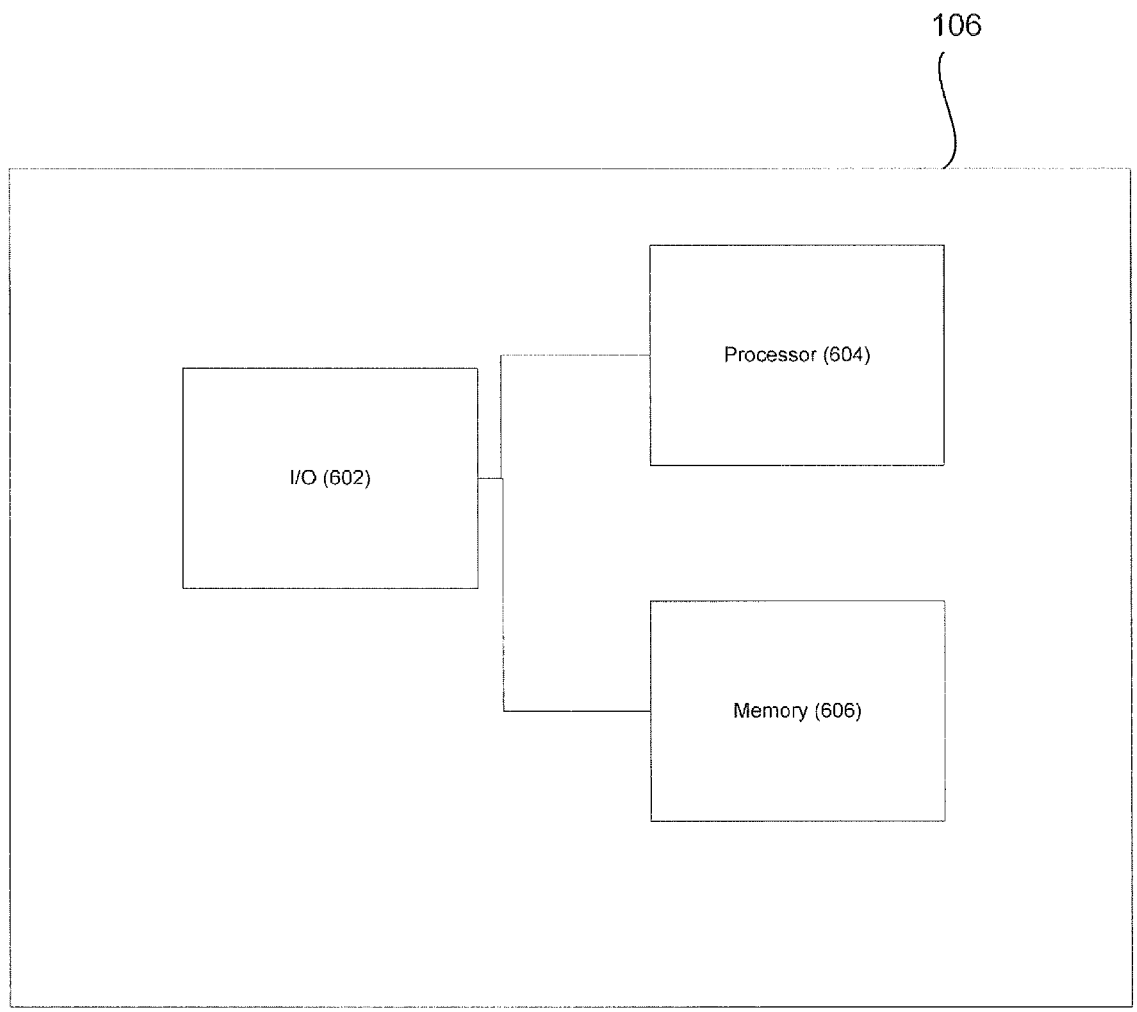
FIG. 6 illustrates example control electronics in a baseline drift correction system according to one embodiment of this disclosure.

FIG. 6 illustrates example control electronics 106 in a baseline drift correction system according to one embodiment of this disclosure. The embodiment of the control electronics 106 shown in FIG. 6 is for illustration only. Other embodiments of the control electronics 106 could be used without departing from the scope of this disclosure.

In this example, the control electronics 106 include an input/output (I/O) 602, a processor 604, and a memory 606. The I/O 602 can be used to receive information from the sensor 104 and report information relating to the results of the sensor analysis. The memory 606 can be used to store information related the analyte being detected. The memory 606 may include information such as the temperature profile of the analyte, as well as information relating to other characteristics of the analyte. The processor 604 can accept input signals from the I/O 602 and determine the concentration of the analyte within the sample. The I/O 602 includes any suitable interface for transmitting and/or receiving data, such as a serial or parallel interface. The processor 604 includes any suitable computing or processing device, such as a microprocessor, microcontroller, FPGA, ASIC, or other component (s). The memory 606 includes any suitable volatile and/or non-volatile storage and retrieval device(s).

Although FIG. 6 illustrates example control electronics 106 in a baseline drift correction system, various changes may be made to FIG. 6. For example, the functions of the control electronics 106 could be implemented in any suitable hardware, software, firmware, or combination thereof.

In some embodiments, various functions described above are implemented or supported by a computer program that is formed from computer readable program code and that is embodied in a computer readable medium. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory.

It may be advantageous to set forth definitions of certain words and phrases used throughout this patent document. The terms "include" and "comprise," as well as derivatives thereof, mean inclusion without limitation. The term "or" is inclusive, meaning and/or. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like. The term "controller" means any device, system, or part thereof that controls at least one operation. A controller may be implemented in hardware, firmware, software, or some combination of at least two of the same. The functionality associated with any particular controller may be centralized or distributed, whether locally or remotely.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. A method comprising:
   acquiring a chemical sample;
   modulating the chemical sample at a frequency greater than a drift frequency of a sensor to produce a modulated chemical sample; and
   determining at least one of a presence and a concentration of an analyte within the modulated chemical sample using the sensor;
   wherein modulating the chemical sample comprises repeatedly heating and cooling a sorbent material to cause the sorbent material to repeatedly absorb and release a portion of the analyte;
   wherein the absorption of the portion of the analyte by the sorbent material decreases an amount of the analyte in the modulated chemical sample provided to the sensor through a flow channel, and the release of the portion of the analyte from the sorbent material increases the amount of the analyte in the modulated chemical sample provided to the sensor through the flow channel;
   wherein the repeated absorption and release of the portion of the analyte causes the amount of the analyte in the modulated chemical sample provided to the sensor to oscillate above and below an actual amount of the analyte in the acquired chemical sample; and
   wherein determining at least one of the presence and the concentration of the analyte within the modulated chemical sample comprises measuring the amount of the analyte in the modulated chemical sample above and below the actual amount of the analyte in the acquired chemical sample.

2. The method of claim 1, wherein:
   the sorbent material absorbing the portion of the analyte causes the concentration of the analyte within the modulated chemical sample provided to the sensor to be lower than an actual concentration of the analyte within the acquired chemical sample; and
   the sorbent material releasing the portion of the analyte causes the concentration of the analyte within the modulated chemical sample provided to the sensor to be higher than the actual concentration of the analyte within the acquired chemical sample.

3. The method of claim 1, wherein modulating the chemical sample comprises repeatedly:
   absorbing part of the analyte into the sorbent material;
   passing a remaining portion of the analyte to the sensor;
   heating the sorbent material;
   releasing the part of the analyte from the sorbent material;
   passing the released part of the analyte to the sensor; and
   passively cooling the sorbent material by stopping the heating of the sorbent material.

4. The method of claim 1, wherein acquiring the chemical sample comprises actively drawing the chemical sample into the flow channel using a pump.

5. The method of claim 1, wherein modulating the chemical sample comprises repeatedly:
   absorbing part of the analyte into the sorbent material;
   passing a remaining portion of the analyte to the sensor;
   heating the sorbent material;
   releasing the part of the analyte from the sorbent material;
   passing the released part of the analyte to the sensor; and
   actively cooling the sorbent material.

6. The method of claim 1, wherein determining at least one of the presence and the concentration of the analyte comprises:
   determining a maximum concentration of the analyte in the modulated chemical sample, the maximum concentration higher than an actual concentration of the analyte in the acquired chemical sample; and
   determining a minimum concentration of the analyte in the modulated chemical sample, the minimum concentration lower than the actual concentration of the analyte in the acquired chemical sample; and
   further comprising determining the actual concentration of the analyte in the acquired chemical sample by applying the minimum and maximum concentrations to a known distribution of concentrations.

7. The method of claim 6, wherein determining the actual concentration of the analyte further comprises:
   adjusting an estimated concentration based on a temperature profile of the analyte.

8. The method of claim 7, wherein the sorbent material is selected based upon the temperature profile of the analyte.

9. A system comprising:
   a pump configured to obtain a chemical sample;
   a pulse generator configured to modulate the chemical sample to produce a modulated chemical sample;
   a sensor configured to detect a concentration of an analyte within the modulated chemical sample, wherein the pulse generator is configured to modulate the chemical sample to produce the modulated chemical sample at a frequency greater than a drift frequency of the sensor; and a controller configured to determine an actual concentration of the analyte within the obtained chemical sample based on an output of the sensor;

wherein the pulse generator is configured to modulate the chemical sample by repeatedly heating and cooling a sorbent material to cause the sorbent material to repeatedly absorb and release a portion of the analyte such that (i) the absorption of the portion of the analyte by the sorbent material decreases an amount of the analyte in the modulated chemical sample provided to the sensor through a flow channel and (ii) the release of the portion of the analyte from the sorbent material increases the amount of the analyte in the modulated chemical sample provided to the sensor through the flow channel;

wherein the pulse generator is configured to modulate the chemical sample so that the amount of the analyte in the modulated chemical sample provided to the sensor oscillates above and below an actual amount of the analyte in the obtained chemical sample; and wherein the controller is configured to determine the actual concentration of the analyte in the obtained chemical sample based on measurements of the amount of the analyte in the modulated chemical sample above and below the actual amount of the analyte in the obtained chemical sample.

10. The system of claim 9, wherein the pulse generator is configured to:

cause the concentration of the analyte within the modulated chemical sample provided to the sensor to be lower than the actual concentration of the analyte within the obtained chemical sample when the sorbent material absorbs the portion of the analyte; and cause the concentration of the analyte within the modulated chemical sample provided to the sensor to be higher than the actual concentration of the analyte within the obtained chemical sample when the sorbent material releases the portion of the analyte.

11. The system of claim 9, wherein the pulse generator further comprises at least one heating element configured to heat the sorbent material.

12. The system of claim 11, wherein the controller is configured to:
- initiate heating of the sorbent material by the at least one heating element so that the sorbent material releases a first part of the analyte and the first part of the analyte is passed to the sensor; and
- stop the heating of the sorbent material by the at least one heating element so that a second part of the analyte is absorbed into the sorbent material and a remaining portion of the analyte is passed to the sensor.

13. The system of claim 9, wherein the sorbent material is designed to absorb only a specific analyte.

14. The system of claim 9, wherein the pump is configured to push the chemical sample into the sensor and to draw the chemical sample out of the sensor.

15. A method comprising:
- acquiring a chemical sample;
- modulating the chemical sample by alternately heating and cooling a sorbent material that alternately releases and absorbs a portion of an analyte in the chemical sample at a frequency higher than a baseline drift of a sensor to produce a modulated chemical sample; and
- determining a concentration of the analyte within the modulated chemical sample using the sensor;

wherein:
- the sorbent material absorbing the portion of the analyte causes the concentration of the analyte within the modulated chemical sample provided to the sensor through a flow channel to be lower than an actual concentration of the analyte in the acquired chemical sample;
- the sorbent material releasing the portion of the analyte causes the concentration of the analyte within the modulated chemical sample provided to the sensor through the flow channel to be higher than the actual concentration of the analyte in the acquired chemical sample;
- the sorbent material repeatedly absorbing and releasing the portion of the analyte causes the concentration of the analyte within the modulated chemical sample provided to the sensor to oscillate above and below the actual concentration of the analyte in the acquired chemical sample; and
- determining the concentration of the analyte within the modulated chemical sample comprises measuring the concentration of the analyte in the modulated chemical sample above and below the actual concentration of the analyte in the acquired chemical sample.

16. The method of claim 15, wherein acquiring the chemical sample comprises actively drawing the chemical sample into the flow channel using a pump.

17. The method of claim 15, wherein determining the concentration of the analyte comprises:
- determining a maximum concentration of the analyte in the modulated chemical sample, the maximum concentration higher than the actual concentration of the analyte in the acquired chemical sample; and
- determining a minimum concentration of the analyte in the modulated chemical sample, the minimum concentration lower than the actual concentration of the analyte in the acquired chemical sample; and
- further comprising determining the actual concentration of the analyte in the acquired chemical sample by applying the minimum and maximum concentrations to a known distribution of concentrations.

18. The method of claim 17, wherein determining the actual concentration of the analyte further comprises:
- adjusting an estimated concentration based on a temperature profile of the analyte.

19. The method of claim 18, further comprising:
- outputting the actual concentration of the analyte.

20. The method of claim 15, wherein modulating the chemical sample comprises repeatedly:
- absorbing part of the analyte into the sorbent material;
- passing a remaining portion of the analyte to the sensor;
- heating the sorbent material;
- releasing the part of the analyte from the sorbent material;
- passing the released part of the analyte to the sensor; and
- passively or actively cooling the sorbent material.

21. The method of claim 1, wherein:
- determining at least one of the presence and the concentration of the analyte comprises obtaining measurements of the analyte within the modulated chemical sample;
- the measurements of the analyte comprise concentrations of the analyte that alternate between higher and lower measurements;
- the higher measurements comprise measurements higher than an actual concentration of the analyte in the acquired chemical sample; and
- the lower measurements comprise measurements lower than the actual concentration of the analyte in the acquired chemical sample.

22. An apparatus comprising:
- a pulse generator configured to modulate a chemical sample to produce a modulated chemical sample; and
- a sensor configured to detect at least one of a presence and a concentration of an analyte within the modulated chemical sample;
- wherein the pulse generator is configured to modulate the chemical sample by repeatedly heating and cooling a sorbent material to cause the sorbent material to repeatedly absorb and release a portion of the analyte such that (i) the absorption of the portion of the analyte by the sorbent material decreases an amount of the analyte in the modulated chemical sample provided to the sensor through a flow channel and (ii) the release of the portion of the analyte from the sorbent material increases the amount of the analyte in the modulated chemical-sample provided to the sensor through the flow channel;
- wherein the pulse generator is configured to modulate the chemical sample so that the amount of the analyte in the modulated chemical sample provided to the sensor varies above and below an actual amount of the analyte in the chemical sample; and
- wherein the sensor is configured to measure the amount of the analyte in the modulated chemical sample above and below the actual amount of the analyte in the chemical sample.

\* \* \* \* \*